United States Patent
Lee et al.

(10) Patent No.: US 8,305,074 B2
(45) Date of Patent: Nov. 6, 2012

(54) MAGNETOSTRICTIVE TRANSDUCER AND APPARATUS AND METHOD FOR MONITORING STRUCTURAL HEALTH USING THE SAME

(75) Inventors: Ju Seung Lee, Pohang-si (KR); Min Kyung Lee, Seoul (KR); Heung Son Lee, Hwaseong-si (KR); Yoon Young Kim, Seoul (KR)

(73) Assignee: SNU R&DB Foundation, Seoul (KR)

( * ) Notice: Subject to any disclaimer, the term of this patent is extended or adjusted under 35 U.S.C. 154(b) by 329 days.

(21) Appl. No.: 12/816,760

(22) Filed: Jun. 16, 2010

(65) Prior Publication Data

US 2010/0321009 A1    Dec. 23, 2010

(30) Foreign Application Priority Data

Jun. 23, 2009    (KR) .................. 10-2009-0055982

(51) Int. Cl.
 *G01B 7/14* (2006.01)
 *G01R 33/18* (2006.01)
 *G01N 27/82* (2006.01)
(52) U.S. Cl. .................. 324/209; 324/207.13; 324/228; 324/240
(58) Field of Classification Search .................. 324/209, 324/207.13, 228, 240
 See application file for complete search history.

(56) References Cited

U.S. PATENT DOCUMENTS

| | | | | |
|---|---|---|---|---|
| 6,924,642 | B1 * | 8/2005 | Cho et al. | 324/240 |
| 7,215,118 | B2 * | 5/2007 | Park et al. | 324/238 |
| 7,614,313 | B2 * | 11/2009 | Kim et al. | 73/862.333 |
| 7,621,189 | B2 * | 11/2009 | Kim et al. | 73/862.335 |

* cited by examiner

*Primary Examiner* — Reena Aurora
(74) *Attorney, Agent, or Firm* — Kile Park Goekjian Reed & McManus PLLC

(57) ABSTRACT

A magnetostrictive transducer that generates a large shear horizontal (SH) wave useful for non-destructive testing of a plate member, and method and apparatus for structural health monitoring by using the magnetostrictive transducer. The magnetostrictive transducer includes: a magnetostrictive patch array comprising a plurality of magnetostrictive patches that have different radii of curvature, and have the same center of curvature when arranged on a plate member and form an overall fan-shape; a static magnetic field forming unit comprising two magnets that are respectively installed on both sides of the magnetostrictive patch so that a magnetic field is formed in parallel to an arc direction of the magnetostrictive patch; and a dynamic magnetic field forming unit comprising a wound coil comprising a plurality of curved portions.

13 Claims, 10 Drawing Sheets

MAGNETOSTRICTIVE TRANSDUCER AND APPARATUS AND METHOD FOR MONITORING STRUCTURAL HEALTH USING THE SAME

CROSS-REFERENCE TO RELATED PATENT APPLICATION

This application claims the benefit of Korean Patent Application No. 10-'9-0055982, filed on Jun. 23, 2009, in the Korean Intellectual Property Office, the disclosure of which is incorporated herein in its entirety by reference.

BACKGROUND OF THE INVENTION

1. Field of the Invention

The present invention relates to a magnetostrictive transducer that generates an elastic ultrasound wave in a plate member or measures the same and an apparatus of monitoring structural health using the magnetostrictive transducer, and more particularly, to a magnetostrictive transducer that generates a large shear horizontal (SH) wave by using magnetostriction, and an apparatus and method for monitoring structural health by using the magnetostrictive transducer.

The present invention is derived from a research project sponsored by the Korea Science and Engineering Foundation and Seoul National University R&DB Foundation.

[2009-0083279, Multi-Scale Paradigm for Creative Design of Multi-Physical Complex Structure System].

2. Description of the Related Art

Magnetostriction refers to mechanical deformation of ferromagnetic materials when the ferromagnetic materials are in a magnetic field. It is also referred as Joule effect. An inverse effect thereof is referred as an inverse magnetostrictive effect or Villari effect in which a magnetic state of a material changes when stress is applied thereto.

A magnetostrictive transducer may be used to measure deformation of an object without mechanically contacting the object, and is thus widely employed in various fields where contact type sensors cannot be used. When using magnetostriction, an elastic wave may be generated contactlessly, and furthermore, a larger elastic guided wave may be generated compared to the case when using the conventional piezoelectric effect.

In general, a guided wave in a thin plate member is classified as a Lamb wave or a shear horizontal (SH) wave according to a vibration method of particles. The SH wave refers to an elastic wave along which particles vibrate perpendicularly in a propagating direction of the wave through a horizontal plane of a plate member. In particular, in a first mode of the SH wave, the SH wave propagates without colliding with an upper or lower boundary, and thus there is no particle dispersion and the SH wave can be transmitted with high efficiency. Thus, the SH wave may be effectively used in non-destructive testing of the plate member.

FIGS. 1 and 2 schematically illustrate deformation of a ferromagnetic material due to magnetostriction.

Referring to FIG. 1, when a first magnetic field $B_S$ and a second magnetic field $B_D$ are applied perpendicularly to each other in the vicinity of a magnetic deformation body 1, the magnetic deformation body 1 may be deformed in a shearing direction as illustrated in FIG. 2. That is, the first magnetic field $B_S$ is a static magnetic field, which remains constant without any variation in the intensity thereof, and the second magnetic field $B_D$ is a dynamic magnetic field. Thus, the magnetic deformation body 1 is deformed according to the variation in the magnetic field of the second magnetic field $B_D$ as illustrated in FIG. 2.

According to the conventional art, it is difficult to generate a large SH wave in a plate member. A small SH wave may be generated in a plate member, but a width thereof is small and the SH wave is transmitted almost linearly only in a predetermined direction. Thus, a small SH wave is not useful for monitoring a defect position in a plate member over a large area. In addition, it is difficult to adjust a frequency at which the SH wave is generated.

SUMMARY OF THE INVENTION

The present invention provides a magnetostrictive transducer that generates a shear horizontal (SH) wave in a plate member to be tested in a non-destructive manner, wherein the SH wave is large and a frequency at which the SH wave is generated may be adjusted.

The present invention also provides a method and apparatus for monitoring structural health of a plate member, whereby a two-dimensional testing can be conducted on a large-sized plate member by using the magnetostrictive transducer.

According to an aspect of the present invention, there is provided a magnetostrictive transducer comprising: a magnetostrictive patch that is attached to a surface of a plate member and has a plane fan-shape; a static magnetic field forming unit comprising two magnets that are respectively installed on both sides of the magnetostrictive patch so that a magnetic field is formed in parallel to an arc direction of the magnetostrictive patch; and a dynamic magnetic field forming unit comprising a wound coil comprising a plurality of curved portions, wherein each of the curved portions of the dynamic magnetic field forming unit has a shape that extends in parallel to an arc direction and corresponds to each of divided portions of the magnetostrictive patch in a parallel direction to an arc of the magnetostrictive patch, and the curved portions are separated apart from one another in a radius direction with respect to a center point of the magnetostrictive patches, and a direction in which the coil is wound differs between the curved portions that are adjacent to another, and thus a direction of a magnetic field formed by the coil differs between the adjacent curved portions when current flows through the coil.

According to another aspect of the present invention, there is provided a magnetostrictive transducer comprising: a magnetostrictive patch array comprising a plurality of magnetostrictive patches that have different radii of curvature, and have the same center of curvature when arranged on a plate member and form an overall fan-shape; a static magnetic field forming unit comprising two magnets that are respectively installed on both sides of the magnetostrictive patches so that a magnetic field is formed in parallel to an arc direction of the magnetostrictive patches; and a dynamic magnetic field forming unit comprising a wound coil comprising a plurality of curved portions, wherein each of the curved portions of the dynamic magnetic field forming unit has a shape that extends in parallel to an arc direction and corresponds to the shape of the magnetostrictive patch in a parallel direction to an arc of the magnetostrictive patch, and the curved portions are separated apart from one another in a radius direction with respect to a center point of the magnetostrictive patches, and a direction in which the coil is wound differs between the curved portions that are adjacent to another, and thus a direction of a magnetic field formed by the coil differs between the adjacent curved portions when current flows through the coil.

The dynamic magnetic field forming unit comprises a plurality of bobbins that are arranged in parallel to an arc direction of the magnetostrictive patch, and the curved portions of the coil are wound along a circumferential surface of the bobbins.

The bobbins are connected to a housing.

Distances between center lines of the bobbins correspond to a half of a wavelength of a generated ultrasonic wave.

The dynamic magnetic field forming unit includes a circuit comprising a coil in a stack type printed circuit board (PCB) including a plurality of PCBs.

The dynamic magnetic field forming unit comprises a plurality of bobbins arranged in parallel to an arc direction of the magnetostrictive transducer, the curved portions of the coil are wound around a circumferential surface of the bobbins, and the magnetostrictive patches are respectively disposed below the coil between the bobbins at a predetermined distance below the bobbins.

According to another aspect of the present invention, there is provided a structural health monitoring apparatus comprising at least two magnetostrictive transducers selected from the group consisting of the above mentioned magnetostrictive transducers.

According to another aspect of the present invention, there is provided a method of monitoring structural health of a plate member, the method comprising: installing at least two magnetostrictive transducers on a plate member at predetermined intervals from each other; selecting one of the magnetostrictive transducers as a transmitter, selecting at least one of the rest of the magnetostrictive transducers as a sensor, generating a ultrasonic wave in the magnetostrictive transducer selected as the transmitter, and sensing the ultrasonic wave using the at least one magnetostrictive transducer selected as the sensor; and determining a defect position from the measured results from the at least one magnetostrictive transducer selected as the sensor.

According to the magnetostrictive transducer of the present invention, a large SH wave may be generated, and a frequency of the generated SH wave may be adjusted. By generating a large SH wave that is transmitted over a broad area, a structural health of a plate member over a broad area may be accurately and simply monitored.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

A magnetostrictive transducer according to an embodiment of the present invention includes a magnetostrictive patch that is attached to a plate member, a static magnetic field forming unit that forms a static magnetic field in the magnetostrictive patch, and a dynamic magnetic field forming unit that forms a dynamic magnetic field in the magnetostrictive patch.

The magnetostrictive patch or the dynamic magnetic field forming unit has a fan-shape. In the magnetostrictive transducer according to the current embodiment, a magnetic field of the dynamic magnetic field forming unit is changed to generate magnetostriction in the magnetostrictive patch so that a shear horizontal (SH) wave is transmitted along the plate member. As the magnetostrictive patch or the dynamic magnetic field forming unit have a fan-shape, the SH wave may be transmitted over a broad area.

The present invention will now be described more fully with reference to the accompanying drawings, in which exemplary embodiments of the present invention are shown.

Figure 1:
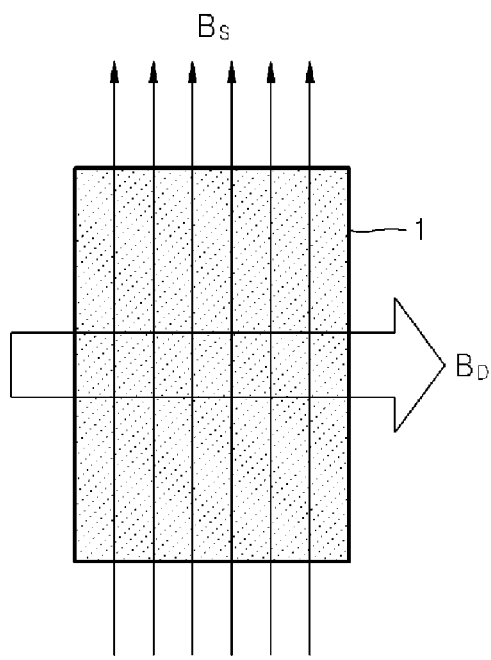
FIGS. 1 and 2 schematically illustrate deformation of a ferromagnetic material due to magnetostriction.
Figure 2:
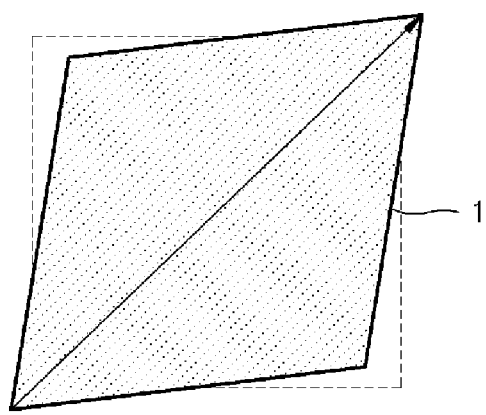
Figure 3:
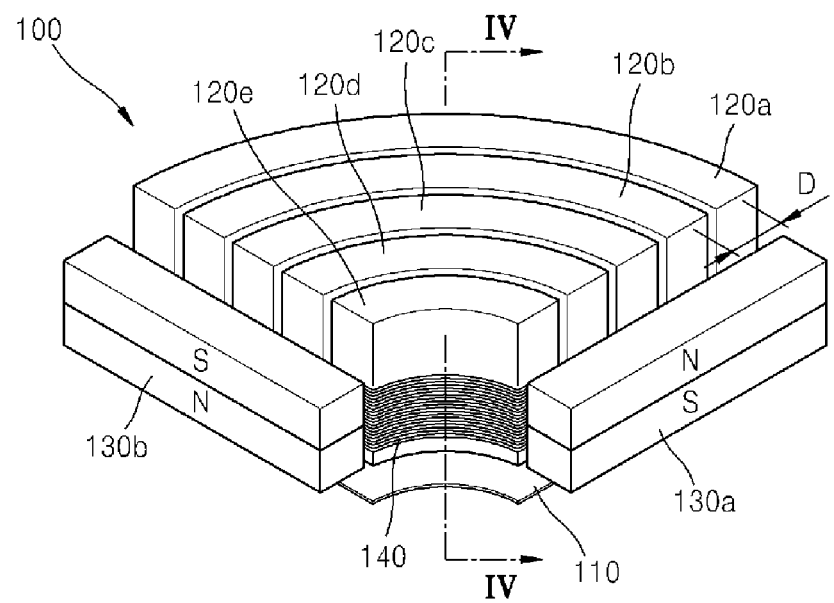
FIG. 3 is a schematic view illustrating a magnetostrictive transducer according to an embodiment of the present invention.
Figure 4:
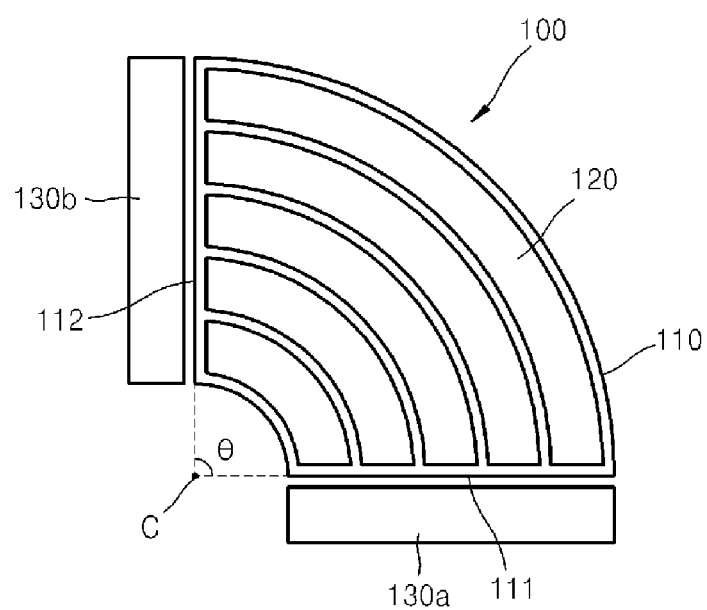
FIG. 4 is a plan view illustrating the magnetostrictive transducer of FIG. 3 (coil is omitted)
Figure 5:
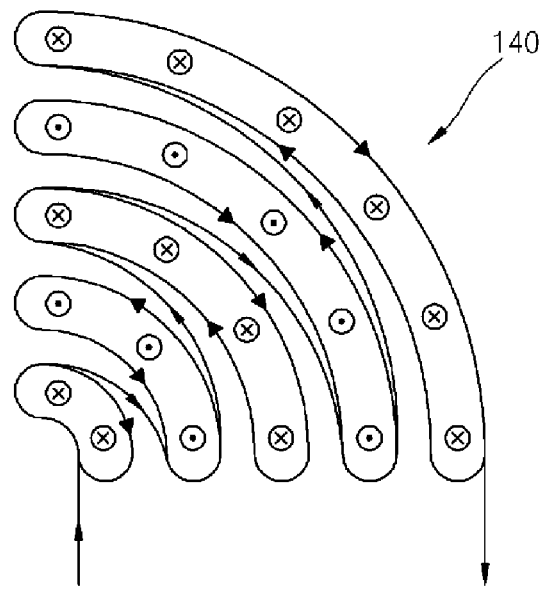
FIG. 5 illustrates a direction in which a coil is wound.

FIG. 3 is a schematic view illustrating a magnetostrictive transducer 100 according to an embodiment of the present invention. FIG. 4 is a plan view illustrating the magnetostrictive transducer of FIG. 3. FIG. 5 illustrates a direction in which a coil is wound around bobbins of the magnetostrictive transducer 100.

Referring to FIG. 3, the magnetostrictive transducer 100 includes a magnetostrictive patch 110, a plurality of bobbins 120, a static magnetic field forming unit, and a dynamic magnetic field forming unit.

The magnetostrictive patch 110 is attached to a surface of a plate member using an adhesive or the like. The magnetostrictive patch 110 is formed of a ferromagnetic body such as Fe, Co, or Ni, or an alloy, and has a fan-shape from which a portion around the center of curvature C is removed as illustrated in FIG. 4. An angle θ between two sides of the magnetostrictive patch 110 with respect to the center of curvature C in FIG. 4 may vary. However, the angle θ may be substantially equal to 90 degrees when used to detect a defect in a large-sized plate member so as to detect the defect by efficiently dividing the large-sized plate member; however, the current embodiment is not limited thereto. Accordingly, a defect may be detected by efficiently covering a broad area of a large-sized plate member. Also, the magnetostrictive patch 110 may be fan-shaped with a portion around the center of curvature C cut out.

The static magnetic field forming unit forms a magnetic field in the circular direction of the magnetostrictive patch 110, and may include two magnets 130a and 130b that are respectively installed at two sides 111 and 112 of the magnetostrictive patch 110. The magnets 130a and 130b may be permanent magnets considering the manufacturing costs and stable measurement of a system (e.g., noise reduction). Also, as illustrated in FIG. 3, the N and S poles of the magnets 130a and 130b may be respectively arranged in a vertical direction, and the N pole of the magnet 130a may be in the same plane with the S pole of the magnet 130b or vice versa.

The bobbins 120 are arranged in parallel to the circular direction of the magnetostrictive patch 110. Referring to FIG. 4, the bobbins 120 have different radii of curvature but centers of each curvature thereof are substantially the same. Thus, the bobbins 120 are overall arranged in a fan-shape. The fan-shapes of the magnetostrictive patch 110 and the bobbins 120 are approximately the same, and an angle between two sides of each of the shapes is substantially the same.

The bobbins 120 may be formed of an insulator such as a polymer material, but they are not limited thereto. For example, the bobbins 120 may be formed of stack type PCBs. A method of forming a closed curve type coil on stack type PCBs will be described below with reference to another embodiment of the present invention.

The dynamic magnetic field forming unit includes a coil 140 that is wound along a circumferential surface of the bobbins 120. A direction in which the coil 140 is wound varies significantly according to the current embodiment of the present invention. The wounding direction of the coil 140 is varies between adjacent bobbins 120, and thus directions of a magnetic field formed by the coil 140 vary between the adjacent bobbins 120 when current flows through the coil 140. For example, referring to FIG. 5, the coil 140 is wound around a smallest first bobbin 120e in a clockwise direction, around a second bobbin 120d in a counterclockwise direction, around a third bobbin 120c in a clockwise direction, around a fourth bobbin 120d in a counterclockwise direction, and around a fifth bobbin 120e in a clockwise direction. When the coil 140 is wound around the bobbins 120 as described above and current flows through the coil 140, a magnetic field is formed in the coil 140 in a direction perpendicular to ground in the bobbins 120e, 120c, and 120a around which the coil 140 is wound in a clockwise direction, and a magnetic field is formed in the coil 140 in a direction perpendicular from the ground of the bobbins 120b and 120d around which the coil is wound in a counterclockwise direction. By adjusting current flowing through the coil 140, the intensity of the magnetic field formed by the coil 140 may be varied.

Meanwhile, by adjusting distances between the bobbins 120, a frequency of an ultrasonic wave generated in the magnetostrictive transducer 100 according to the current embodiment of the present invention may be adjusted.

Hereinafter, an operation of the magnetostrictive transducer 100 having the above-described structure will be described with reference to FIGS. 6 and 7.

Figure 6:
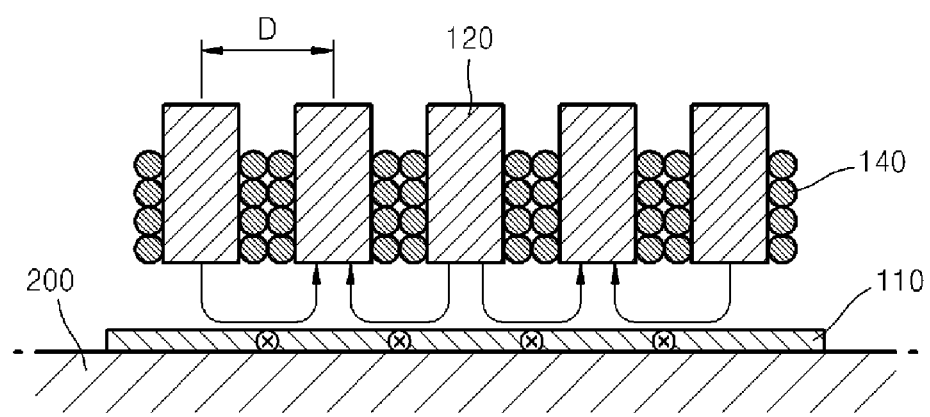
FIG. 6 is a cross-sectional view illustrating the magnetostrictive transducer cut along a line VI-VI.
Figure 7:
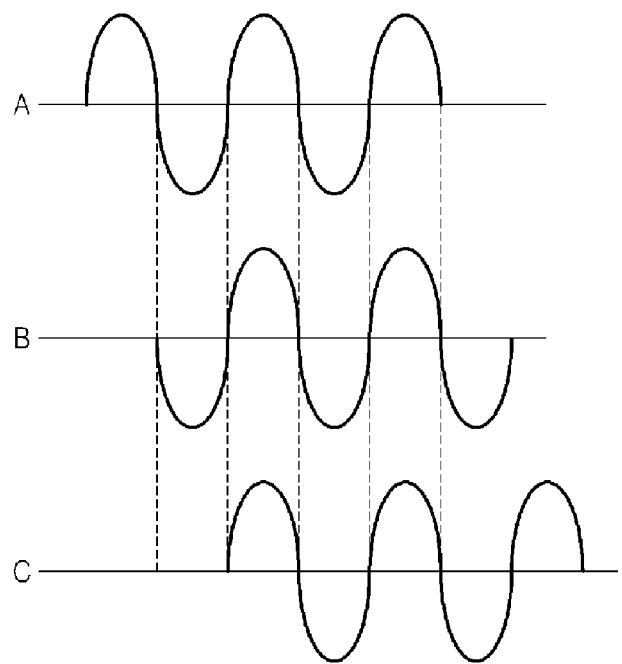
FIG. 7 is a schematic view illustrating superposition of waves generated in a magnetostrictive transducer according to an embodiment of the present invention.

FIG. 6 is a cross-sectional view illustrating the magnetostrictive transducer 100 of FIG. 3 cut along a line VI-VI. FIG. 7 is a schematic view illustrating superposition of waves generated in the magnetostrictive transducer 100.

Referring to FIG. 6, a static magnetic field is formed in the magnetostrictive patch 110 in a predetermined direction by the static magnetic field forming unit. Then, when current flows through the coil 140, a magnetic field is formed in a direction as indicated by an arrow, and by adjusting the current flowing through the coil 140, the magnetic field indicated by the arrow becomes a dynamic magnetic field. Multiple points exist in the magnetostrictive patch 110 where a static magnetic field and a dynamic magnetic field perpendicularly cross each other, and accordingly, the magnetostrictive patch 110 is partially deformed by magnetostriction and thus a wave is generated in the magnetostrictive patch 110. The wave is an SH wave useful for testing a defect in a plate member, is different from other types of noise, and is transmitted to the plate member attached to the magnetostrictive patch 110.

As can be seen from FIG. 6, when the coil 140 is wound around five bobbins 120, an SH wave is generated at four points, which is one less than the number of the bobbins 120. In order that SH waves are effectively used in detecting a defect position of a plate member, the SH waves may be superposed over one another so as to increase an output of the magnetostrictive transducer 100. The superposition of the SH waves may be realized by adjusting a distance D between the bobbins 120. The SH waves generated at four points in FIG. 6 have opposite vibration directions with respect to each of the four points. By adjusting the distance D to be equal to half the wavelength of the SH waves, the SH waves generated at each point may be superposed and strengthened due to constructive interference. That is, an SH wave generated at a point (i) and an SH wave generated at a point (ii) adjacent to the point (i) have opposite phases. When a phase difference of the two SH waves corresponds to half the wavelength, the waves generated at the two points (i) and (ii) substantially have the same phase and thus are superposed over each other, and become a larger SH wave due to constructive interference. In this manner, the SH waves respectively generated at the four points generate a constructive interference with one another, and thus an output of the magnetostrictive transducer 100 according to the current embodiment of the present invention may be significantly increased.

Hereinafter, a method of detecting a defect in a large-sized plate member by using the magnetostrictive transducer according to the current embodiment of the present invention will be described.

Figure 8:
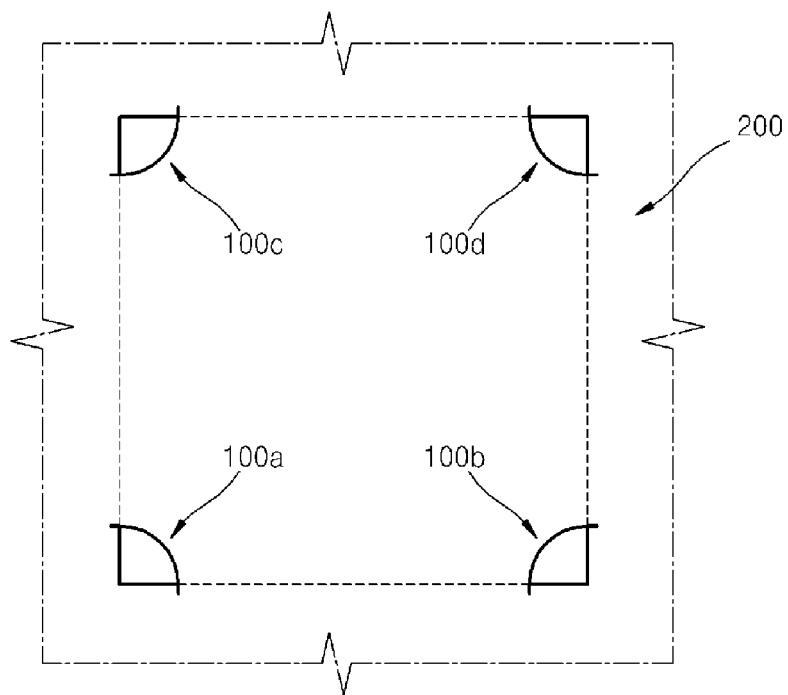
FIG. 8 is a schematic view illustrating an arrangement example of a plurality of magnetostrictive transducers for testing structural defects in a plate member according to an embodiment of the present invention.

FIG. 8 is a schematic view illustrating an arrangement example of a plurality of magnetostrictive transducers for testing structural defects in a plate member according to an embodiment of the present invention, namely an apparatus for monitoring structural health of a plate member 200.

Referring to FIG. 8, magnetostrictive transducers 100a, 100b, 100c, and 100d are installed for form a regular square on a plate member. Also, an angle θ of the fan-shape of each of the magnetostrictive transducers 100a, 100b, 100c, and 100d is 90 degrees, the magnetostrictive transducers 100a, 100b, 100c, and 100d are disposed with the opening of the fan-shape toward the center of the square, and lateral sides of each two adjacent magnetostrictive transducers from the magnetostrictive transducers 100a, 100b, 100c, and 100d are respectively linearly aligned, thereby forming the regular square.

Only one of the magnetostrictive transducers 100a, 100b, 100c, and 100d generates an SH wave. However, when the SH waves are transmitted, an electromotive force is generated in the coil 140 due to the inverse magnetostrictive effect, and the amplitude of the SH wave may be measured by measuring a variation in current flowing through the coil 140, and thus the magnetostrictive transducers 100a, 100b, 100c, and 100d may also be used as sensors.

One of the magnetostrictive transducers 100a, 100b, 100c, and 100d illustrated in FIG. 8 is selected as a transmitter that generates an SH wave, and one or two of the remaining magnetostrictive transducers adjacent to the transmitter is selected to function as a sensor.

The method of testing a defect position will be described in detail below.

In the case of the arrangement of the magnetostrictive transducers 100a, 100b, 100c, and 100d illustrated in FIG. 8, the magnetostrictive transducer 100a is selected as a transmitter, and the two magnetostrictive transducers 100b and 100c adjacent thereto are selected as sensors. The magnetostrictive transducer 100d may not be used since amplitude of a signal reflected by a defect that is sensed by the magnetostrictive transducer 100d is relatively small. For example, a signal that is generated by actuating an SH wave in the magnetostrictive transducer 100a which is received by the magnetostrictive transducer 100b and a signal that is generated by actuating an SH wave in the magnetostrictive transducer 100b which is received by the magnetostrictive transducer 100a are identical. Thus, in the arrangement as illustrated in FIG. 8, in total, four signals are received and used to determine a defect position.

With respect to a signal, when a position of a transmitter is T, and a position of a sensor is S, a length T-P and a length P-S with respect to a position P in a defect testing area may be detected, and thus by using a speed of an SH wave, time the SH wave passes the lengths T-P-S may be calculated. In a time plot of a signal that is received by the sensor, amplitude of the signal corresponding to the above-calculated time is searched for and is marked as a point P with a color. The above operation is repeatedly performed with respect to all positions in the defect testing area to obtain an image.

Figure 16:
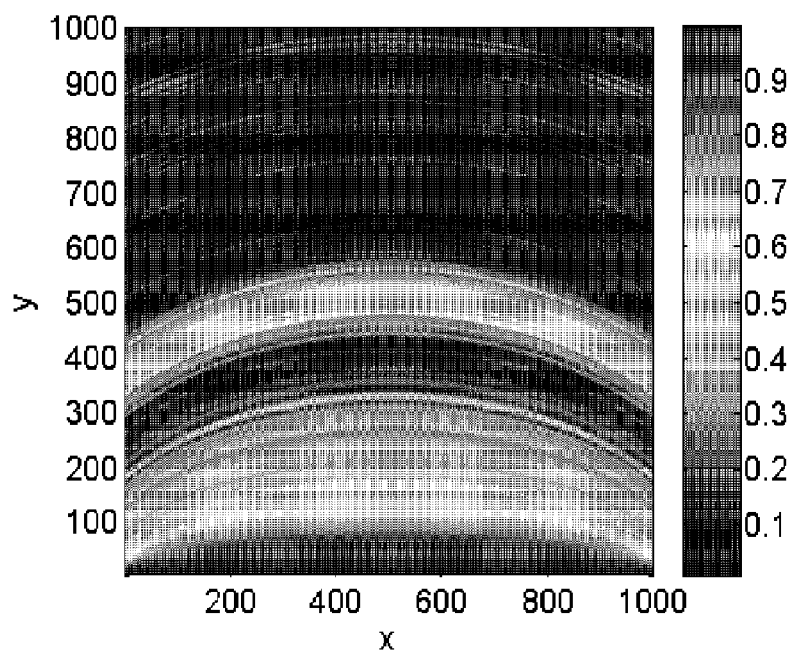
FIGS. 16 and 17 are images illustrating a signal that is transmitted by a transmitter and received by a sensor in an apparatus for monitoring structural health, according to an embodiment of the present invention.
Figure 17:
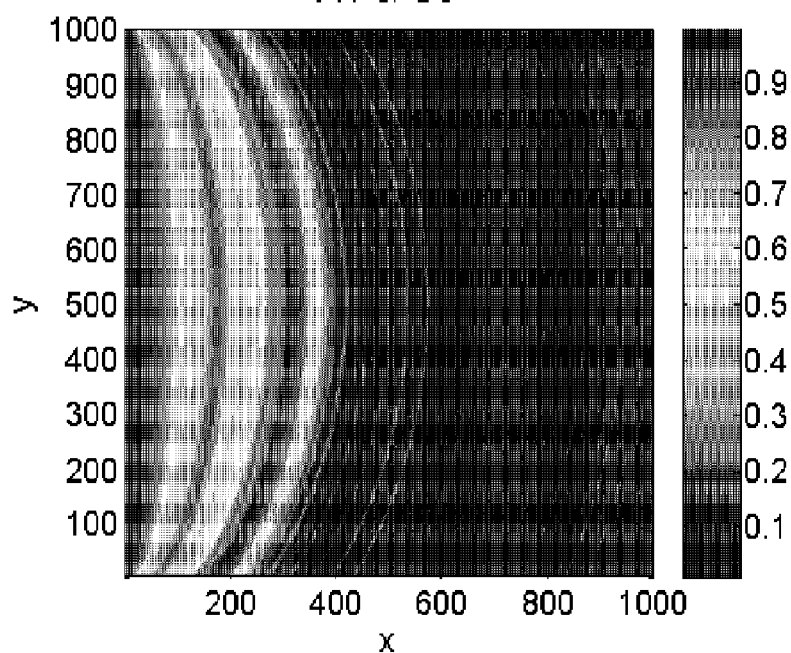

FIG. 16 is an image illustrating a signal that is transmitted by the magnetostrictive transducer 100a and received by the magnetostrictive transducer 100b, and FIG. 17 is an image illustrating a signal that is transmitted by the magnetostrictive transducer 100a and received by the magnetostrictive transducer 100c. An amplitude of a signal that has returned after striking a defect is relatively large, and thus a line formed by connecting a point P, which is a candidate defect position, and the positions T and S forms an ellipse which has the positions T and S as two focal points as illustrated in FIGS. 16 and 17. That is, points on the ellipse may be regarded as candidate defect positions.

Figure 18:
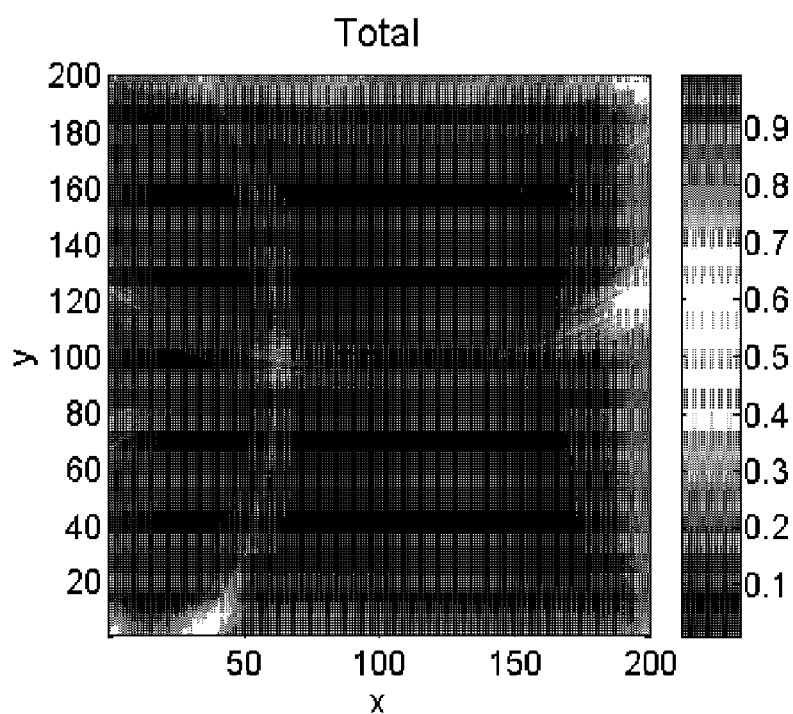
FIG. 18 is an image showing a position of a defect in a plate member determined by superposing the graphs of the signal illustrated in FIGS. 16 and 17.

FIG. 18 is an image showing positions of defects in a plate member by superposing the images illustrated in FIG. 16 or FIG. 17.

Four images are respectively obtained in total from four signals that are respectively measured in the above-described manner, and when the images are superposed, an image as shown in FIG. 18 is obtained. Referring to FIG. 18, we can see cross points of each of ellipses, and these points are defect positions.

Superposing images may be referred to as a method of synthesizing data. However, defect positions may also be determined by using various methods other than the synthesizing method.

Figure 19:
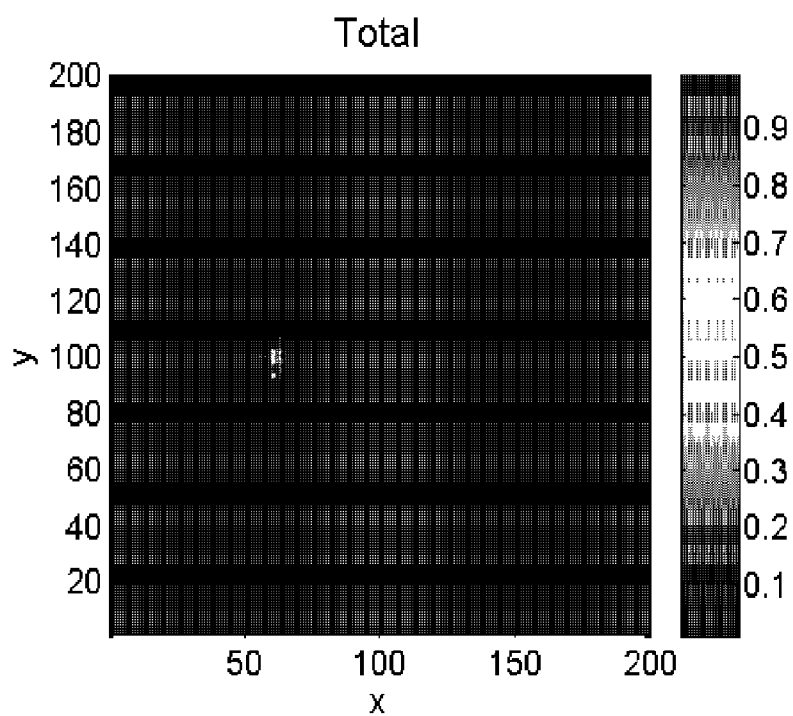
FIG. 19 is an image showing a position of a defect in a plate member determined by multiplying data of the signal of the images of FIGS. 16 and 17.

FIG. 19 is an image showing a position of defects in a plate member determined by multiplying data. As illustrated in FIG. 19, by multiplying data of the above four measured points and displaying a result of the multiplication of the data, the defect positions are clearly displayed on the image.

In addition, the defect positions may also be determined by square-multiplying the amplitudes of each of the signals at each point and multiplying the squares, or by multiplying squares of the amplitudes of the signals.

Meanwhile, referring to FIGS. 3 and 4, the bobbins 120 and the static magnetic field forming unit are respectively separately formed. However, the bobbins 120 may also be formed as a single unit in a separate housing and permanent magnets of the static magnetic field forming unit may be fixed to the housing.

Also, the dynamic magnetic field forming unit may be formed not only by winding a coil to the bobbins; alternatively, the dynamic magnetic field forming unit may also be formed by forming a coil on a stack-type PCB.

Hereinafter, performance evaluation of the magnetostrictive transducer according to the present invention will be described with reference to FIGS. 9 and 10.

Figure 9:
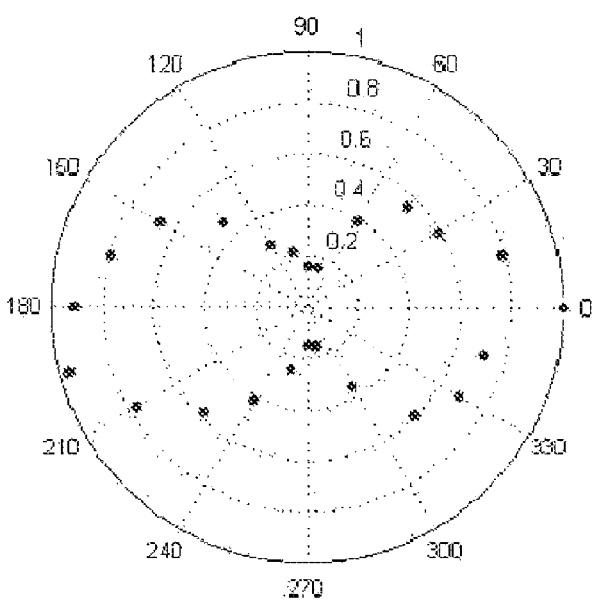
FIG. 9 is a graph showing a radiation pattern of a shear horizontal (SH) wave generated by a magnetostrictive transducer according to an experimental result according to an embodiment of the present invention.
Figure 10:
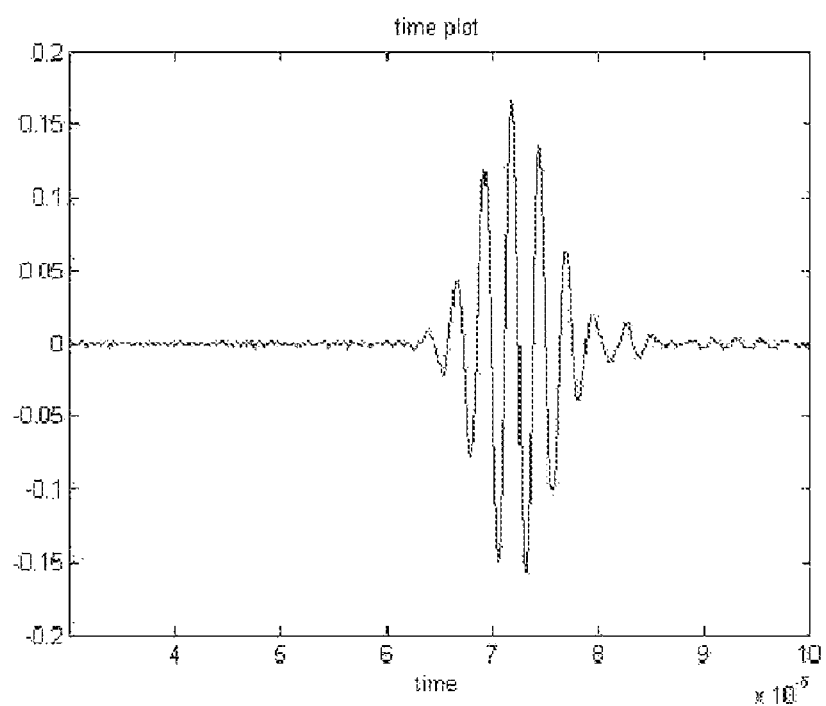
FIG. 10 is an image showing an SH wave that is generated by one of the magnetostrictive transducers arranged as in FIG. 8 and is received by another adjacent magnetostrictive transducer.

FIG. 9 is a graph showing experimental results of a radiation pattern of a shear horizontal (SH) wave generated by a magnetostrictive transducer according to an embodiment of the present invention. FIG. 10 is a signal showing an SH wave generated in a magnetostrictive transducers arranged as in FIG. 8 and transmitted to an adjacent magnetostrictive transducer.

With regard to the experimental results of FIG. 9 and the description of FIG. 3, the angle θ of the magnetostrictive transducer that generates the SH wave is 90 degrees and a side 111 of the magnetostrictive transducer corresponds to a 315-degree line in FIG. 9, and other side 112 corresponds to a 45-degree line in FIG. 9. As can be seen from FIG. 9, the SH wave generated by the magnetostrictive transducer according to the current embodiment of the present invention is transmitted to a large extent within a range of −45 degrees (315 degrees) to +45 degrees, and in a range of −135 degrees (225 degrees) to +135 degrees.

An SH wave may also be generated in a plate member by attaching a meander coil on the plate member and applying current to the meander coil to generate magnetostriction. However, in this case, since the SH wave is generated and measured while being focused in a predetermined direction (a direction toward a dynamic magnetic field), structural health monitoring for determining a defect position in a relatively large range may not be performed in the manner as described with reference to FIG. 8.

However, according to the current embodiment of the present invention, since a fan-shaped magnetostrictive patch or a fan-shaped dynamic magnetic field forming unit is used, an SH wave that is transmitted over a large range may be generated, thereby easily detecting defect positions over a broad range of a plate member.

Also, regarding the method of generating an SH wave by using a meander coil, since the meander coil is arranged in a linear direction, the magnitude of a dynamic magnetic field which causes a dynamic deformation of ferromagnetic materials is very small.

However, according to the current embodiment, a dynamic field can be amplified by increasing the coil turns, and thus an SH wave having a large amplitude may be generated.

Figure 11:
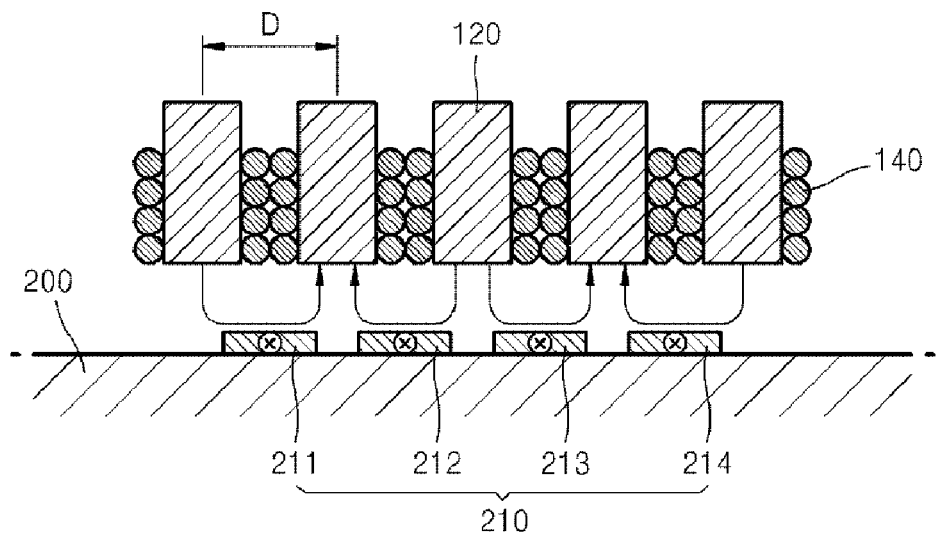
FIG. 11 is a cross-sectional view illustrating a magnetostrictive transducer according to another embodiment of the present invention.

FIG. 11 is a cross-sectional view illustrating a magnetostrictive transducer according to another embodiment of the present invention.

As illustrated in FIG. 11, the magnetostrictive transducer according to the current embodiment is different from the magnetostrictive transducer of the previous embodiment described in FIGS. 3 through 6 in that a magnetostrictive patch array 210 includes a plurality of magnetostrictive patches 211, 212, 213, and 214.

The magnetostrictive patches 211, 212, 213, and 214 are separated at predetermined intervals and attached to a plate member in a fan-shape.

The magnetostrictive patches 211, 212, 213, and 214 in the current embodiment have different radii of curvature and different arc lengths, but are disposed to have the same center of curvature when they are attached to the plate member. Accordingly, the set of the magnetostrictive patch array 210 including the magnetostrictive patches 211, 212, 213, and 214 has a fan-shape.

As illustrated in FIG. 11, the magnetostrictive patches 211, 212, 213, and 214 are respectively disposed below at a predetermined distance from a coil 140 disposed between bobbins 120.

Distances between the magnetostrictive patches 211, 212, 213, and 214 may be substantially equal to distances between the bobbins 120.

In the above structure, the magnetostrictive patches 211, 212, 213, and 214 are attached only positioning a location where magnetostriction is actually generated, and thus the user may select a portion for generating magnetostriction. An operation of installing or manufacturing the magnetostrictive patches 211, 212, 213, and 214 may be complicated compared to the previous embodiment. However, use of a vinyl tape that connects the magnetostrictive patches 211, 212, 213, and 214 may facilitate an installation operation.

Figure 12:
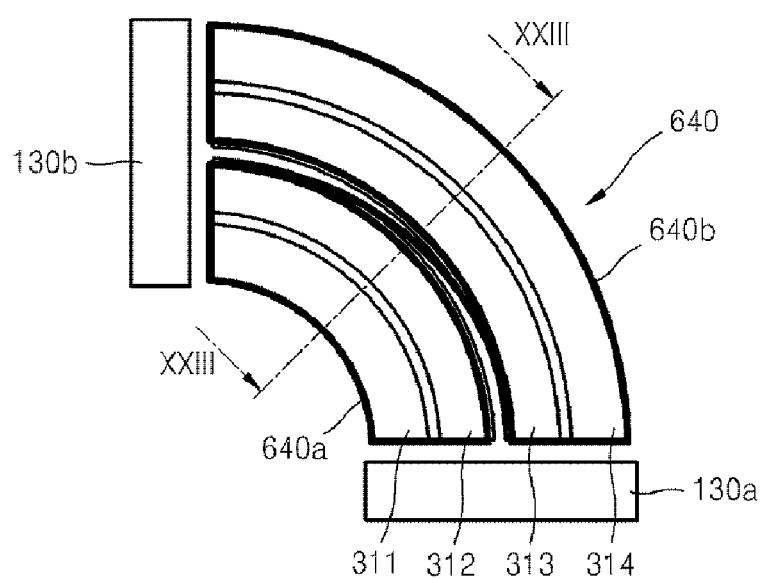
FIG. 12 is a plan view illustrating a magnetostrictive transducer according to another embodiment of the present invention.
Figure 13:
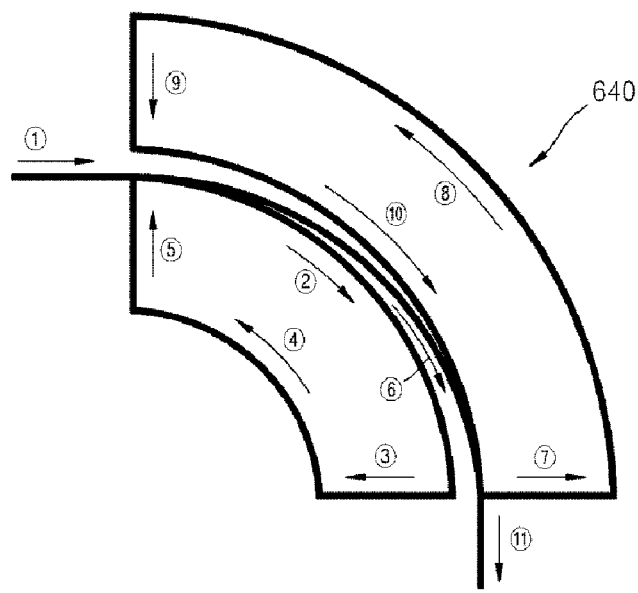
FIG. 13 illustrates a direction in which a figure-of-8 type coil of FIG. 12 is wound.
Figure 14:
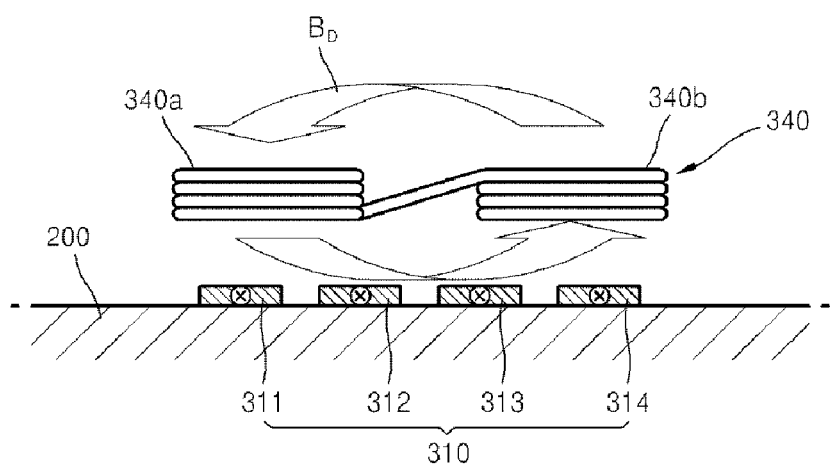
FIG. 14 is a cross-sectional view of the magnetostrictive transducer of FIG. 12 cut along a line XIV-XIV, for explaining the operational principle of the magnetostrictive transducer of FIG. 12.

FIG. 12 is a cross-sectional view illustrating a magnetostrictive transducer according to another embodiment of the present invention. FIG. 13 illustrates a direction in which a figure-of-8 type coil of FIG. 12 is wound. FIG. 14 is a cross-sectional view of the magnetostrictive transducer of FIG. 12 cut along a line XIV-XIV, for explaining the operational principle of the magnetostrictive transducer of FIG. 12.

Referring to FIG. 12, the magnetostrictive transducer includes a figure-of-8 type coil 340 that is used as a dynamic magnetic field forming unit, two magnets 130a and 130b that are used as a static magnetic field forming unit, and a magnetostrictive patch array 310 that has a fan-shape and includes a plurality of magnetostrictive patches 311, 312, 313, and 314 arranged at predetermined intervals.

The magnets 130a and 130b are the same as in one of the previous embodiments.

The configuration of the magnetostrictive patch array 310 is the same as that in the previous embodiment.

The figure-of-8 type coil 340 functions as a dynamic magnetic field forming unit in the current embodiment of the present invention. A plane shape of the figure-of-8 type coil 340 includes a plurality of curved portions having a fan-shape as illustrated in FIGS. 12 and 13. The curved portions are formed along an outer circumferential line of at least one of the magnetostrictive patches 311, 312, 313, and 314. A method of manufacturing the figure-of-8 type coil 340 includes forming a closed curve in a clockwise direction at one side (①②③④⑤⑥), and a closed curve in a counterclockwise direction at the other side (⑦⑧⑨⑩⑪), as illustrated in FIG. 13. When the figure-of-8 type coil 340 is formed as described above and current is applied from a first end portion ① to a second end portion ⑪ in FIG. 13, a magnetic field heading from a closed curve at one side toward a closed curve at the other side is formed as indicated by a large arrow as illustrated in FIG. 14. That is, as illustrated in FIG. 14, a magnetic field is formed perpendicularly to an arc direction of each of the magnetostrictive patches 312, 312, 313, and 314 below the figure-of-8 type coil 340. When the magnetic field is formed as illustrated in FIG. 14, the magnetostriction patches 312, 312, 313, and 314 below the figure-of-8 type coil 340 are deformed in a perpendicular direction to the arc of figure-of-8 type coil 340 due to the magnetostriction. By adjusting current flowing through the figure-of-8 type coil 340, an SH wave is generated and transmitted in a plate member to which the magnetostrictive patches 312, 312, 313, and 314 are firmly attached. Accordingly, we can detect a defect position in the plate member by generating and sensing the SH wave.

Like in the embodiment of FIG. 11, the magnetostrictive patches 312, 312, 313, and 314 are attached only to positions where magnetostriction is actually generated, and thus the user may select an area where magnetostriction is to be generated. Also, a frequency of a generated SH wave may be adjusted.

Meanwhile, compared to the method of generating an SH wave by using a meander coil, when the figure-of-8 type coil 340 is used, the amplitude of SH wave from the figure-of-8 type coil 340 may be increased as in the embodiments of FIGS. 3 through 6 and FIG. 11, and thus the amplitude of a dynamic magnetic field may be increased, and accordingly, a large SH wave may be generated.

Hereinafter, a dynamic magnetic field forming unit formed using a stack type PCB instead of a bobbin will be described with reference to the embodiment of FIGS. 3 through 6.

Figure 15:
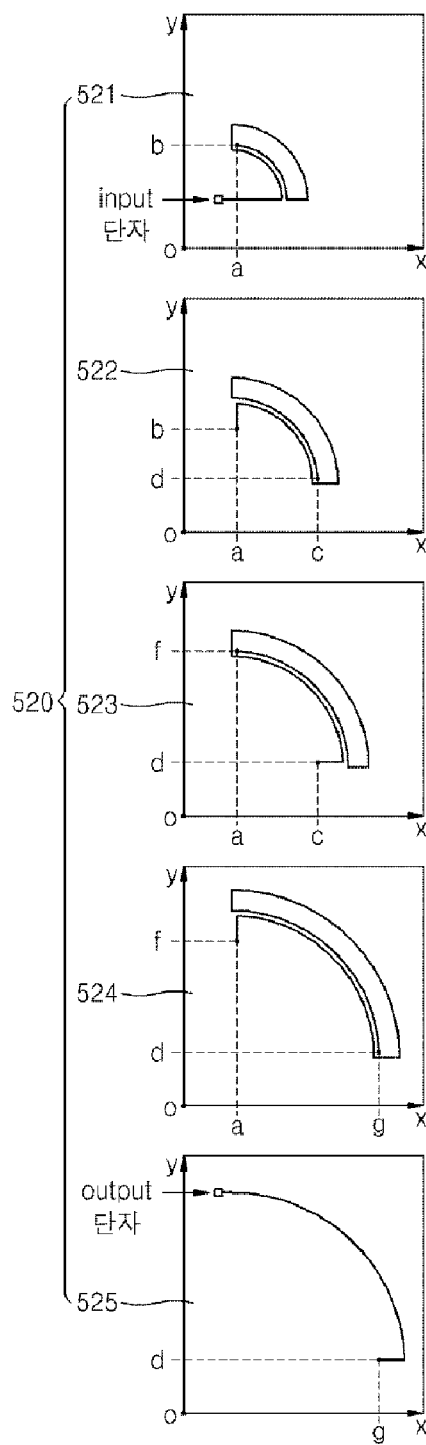
FIG. 15 is a plan view illustrating a dynamic magnetic field used in the embodiment of FIG. 3.

FIG. 15 is a plan view illustrating a dynamic magnetic field forming unit used in the embodiment of FIG. 3, which is formed using a stack type printed circuit board (PCB). In FIG. 15, PCBs to be stacked are illustrated according to the order of stacking.

Compared to the embodiment described with reference to FIGS. 3 through 6, the dynamic magnetic field forming unit formed using the stack type PCBs illustrated in FIG. 15 includes four curved portions of a coil that form the dynamic magnetic field forming unit; however, the number of the curved portions or the number of magnetostrictive patches of a magnetostrictive patch array is not limited thereto.

At least four PCBs need to be stacked to form a dynamic magnetic field forming unit having four curved portions. In FIG. 15, five PCBs are stacked to be a dynamic magnetic field forming unit having four curved portions 520. In FIG. 15, each of the PCBs has the same size, and a circuit formed in each of the PCBs is almost a closed curve but a terminal thereof is not completely closed. A terminal of one PCB needs to be connected to a terminal of another PCB. Thus, in order to connect terminals of different PCBs to one another, the terminals to be connected may be respectively positioned on the same-sized PCBs at the same location on an x-y plane, which corresponds to at an end of the PCB. When the terminals are positioned in this manner, the terminals to be connected are positioned along a vertical direction when the PCBs are stacked, and thus terminals disposed on different PCBs may be electrically simply connected to one another through a via hole.

In this manner, a circuit is formed from an input terminal in a first substrate 521 with a fan-shape not including a starting point O, that is, a shape extended along an arc direction. Next, a terminal at (a, b) of the first substrate 521 is connected to a terminal at (a, b) of a second substrate 522 through a via hole, and a radius of curvature of a curved portion in the second substrate 522 is higher than that of the curved portion of the first substrate 521, and the curved portion of the second substrate 522 is extended to a terminal at (c, d) of the second substrate 522. Next, the terminal at (c, d) of the second substrate 522 is connected to a terminal at (c, d) of a third substrate 523 through a via hole, and a radius of curvature of a curved portion in the third substrate 523 is higher than that of the curved portion of the first substrate 521 than that of the curved portion of the first substrate 521 or the second substrate 522, and the curved portion of the third substrate 523 is extended to a terminal at (a, f) of the third substrate 523. Next, the terminal at (a, f) of the third substrate 523 is connected to a terminal at (a, f) of a fourth substrate 524 through a via hole, and a radius of curvature of a curved portion in the fourth substrate 524 is higher than that of the curved portion of the third substrate 523, and the curved portion of the fourth substrate 524 is extended to a terminal at (g, d) of the fourth substrate 524. Next, the terminal at (g, d) of the fourth substrate 524 is connected to a terminal at (g, d) of a fifth substrate 525 through a via hole. In the fifth substrate 525, a curved portion is extended in the form of an arc up to an output terminal.

Meanwhile, amplitude of a magnetic field formed by the dynamic magnetic field forming unit may be increased by arranging the circuit in each of the PCBs by wounding the circuit several times at small distances.

When the PCBs are stacked as illustrated in FIG. 15 and current is applied thereto from a power source, a magnetic field as illustrated in FIG. 14 may be formed.

The above-described stack type PCBs may be applied not only to the dynamic magnetic forming unit of the embodiment of FIGS. 3 through 6 but also to the separated fan-shaped coil 140 or 340 of the embodiments of FIG. 11 or 12.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A magnetostrictive transducer comprising:
a magnetostrictive patch that is attached to a surface of a plate member and has a plane fan-shape;
a static magnetic field forming unit comprising two magnets that are respectively installed on both sides of the magnetostrictive patch so that a magnetic field is formed in parallel to an arc direction of the magnetostrictive patch; and
a dynamic magnetic field forming unit comprising a wound coil comprising a plurality of curved portions,
wherein each of the curved portions of the dynamic magnetic field forming unit has a shape that extends in parallel to an arc direction and corresponds to each of divided portions of the magnetostrictive patch in a parallel direction to an arc of the magnetostrictive patch, and the curved portions are separated apart from one another in a radius direction with respect to a center point of the magnetostrictive patches, and a direction in which the coil is wound differs between the curved portions that are adjacent to another, and thus a direction of a magnetic field formed by the coil differs between the adjacent curved portions when current flows through the coil.

2. The magnetostrictive transducer of claim 1, wherein the dynamic magnetic field forming unit comprises a plurality of bobbins that are arranged in parallel to an arc direction of the magnetostrictive patch, and the curved portions of the coil are wound along a circumferential surface of the bobbins.

3. The magnetostrictive transducer of claim 2, wherein the bobbins are connected to a housing.

4. The magnetostrictive transducer of claim 2, wherein distances between center lines of the bobbins corresponds to a half of a wavelength of a generated ultrasonic wave.

5. The magnetostrictive transducer of claim 1, wherein the dynamic magnetic field forming unit includes a circuit comprising a coil in a stack type printed circuit board (PCB) including a plurality of PCBs.

6. A magnetostrictive transducer comprising:
a magnetostrictive patch array comprising a plurality of magnetostrictive patches that have different radii of curvature, and have the same center of curvature when arranged on a plate member and form an overall fan-shape;
a static magnetic field forming unit comprising two magnets that are respectively installed on both sides of the magnetostrictive patches so that a magnetic field is formed in parallel to an arc direction of the magnetostrictive patches; and
a dynamic magnetic field forming unit comprising a wound coil comprising a plurality of curved portions,
wherein each of the curved portions of the dynamic magnetic field forming unit has a shape that extends in parallel to an arc direction and corresponds to the shape of the magnetostrictive patch in a parallel direction to an arc of the magnetostrictive patch, and the curved portions are separated apart from one another in a radius direction with respect to a center point of the magnetostrictive patches, and a direction in which the coil is wound differs between the curved portions that are adjacent to another, and thus a direction of a magnetic field formed by the coil differs between the adjacent curved portions when current flows through the coil.

7. The magnetostrictive transducer of claim 6, wherein the dynamic magnetic field forming unit comprises a plurality of bobbins that are arranged in parallel to an arc direction of the magnetostrictive patch, and the curved portions of the coil are wound along a circumferential surface of the bobbins.

8. The magnetostrictive transducer of claim 7, wherein the bobbins are connected to a housing.

9. The magnetostrictive transducer of claim 7, wherein distances between center lines of the bobbins corresponds to a half of a wavelength of a generated ultrasonic wave.

10. The magnetostrictive transducer of claim 6, wherein the dynamic magnetic field forming unit includes a circuit comprising a coil in a stack type printed circuit board (PCB) including a plurality of PCBs.

11. The magnetostrictive transducer of claim 6, wherein the dynamic magnetic field forming unit comprises a plurality of bobbins arranged in parallel to an arc direction of the magnetostrictive transducer, the curved portions of the coil are wound around a circumferential surface of the bobbins, and the magnetostrictive patches are respectively disposed below the coil between the bobbins at a predetermined distance below the bobbins.

12. An apparatus for monitoring structural health of a plate member comprising at least two magnetostrictive transducers,
wherein at least one of the magnetostrictive transducers comprising:
a magnetostrictive patch that is attached to a surface of a plate member and has a plane fan-shape;
a static magnetic field forming unit comprising two magnets that are respectively installed on both sides of the magnetostrictive patch so that a magnetic field is formed in parallel to an arc direction of the magnetostrictive patch; and a dynamic magnetic field forming unit comprising a wound coil comprising a plurality of curved portions, wherein each of the curved portions of the dynamic magnetic field forming unit has a shape that extends in parallel to an arc direction and corresponds to each of divided portions of the magnetostrictive patch in a parallel direction to an arc of the magnetostrictive patch, and the curved portions are separated apart from one another in a radius direction with respect to a center point of the magnetostrictive patches, and a direction in which the coil is wound differs between the curved portions that are adjacent to another, and thus a direction of a magnetic field formed by the coil differs between the adjacent curved portions when current flows through the coil.

13. A method of monitoring structural health of a plate member, the method comprising:

installing at least two magnetostrictive transducers on a plate member at predetermined intervals from each other;

selecting one of the magnetostrictive transducers as a transmitter, selecting at least one of the rest of the magnetostrictive transducers as a sensor, generating a ultrasonic wave in the magnetostrictive transducer selected as the transmitter, and sensing the ultrasonic wave using the at least one magnetostrictive transducer selected as the sensor; and determining a defect position from the measured results from the at least one magnetostrictive transducer selected as the sensor, wherein at least one of the magnetostrictive transducers comprising:

a magnetostrictive patch that is attached to a surface of a plate member and has a plane fan-shape;

a static magnetic field forming unit comprising two magnets that are respectively installed on both sides of the magnetostrictive patch so that a magnetic field is formed in parallel to an arc direction of the magnetostrictive patch; and a dynamic magnetic field forming unit comprising a wound coil comprising a plurality of curved portions, wherein each of the curved portions of the dynamic magnetic field forming unit has a shape that extends in parallel to an arc direction and corresponds to each of divided portions of the magnetostrictive patch in a parallel direction to an arc of the magnetostrictive patch, and the curved portions are separated apart from one another in a radius direction with respect to a center point of the magnetostrictive patches, and a direction in which the coil is wound differs between the curved portions that are adjacent to another, and thus a direction of a magnetic field formed by the coil differs between the adjacent curved portions when current flows through the coil.

* * * * *